United States Patent [19]

McLaughlin

[11] Patent Number: 4,785,969
[45] Date of Patent: Nov. 22, 1988

[54] MEDICATION DISPENSING SYSTEM

[75] Inventor: John T. McLaughlin, Costa Mesa, Calif.

[73] Assignee: Pyxis Corporation, Newport Beach, Calif.

[21] Appl. No.: 928,809

[22] Filed: Nov. 10, 1986

[51] Int. Cl.⁴ .............................................. B65D 83/04
[52] U.S. Cl. ........................................... 221/2; 221/15;
221/83; 221/86; 221/79; 221/197; 364/479
[58] Field of Search ......................................... 221/1-5,
221/15, 82, 83, 86, 197, 206, 76, 79, 80, 81;
364/479; 235/380, 381

[56] References Cited

U.S. PATENT DOCUMENTS

| | | | |
|---|---|---|---|
| 3,744,672 | 7/1973 | Dangles et al. | 221/82 |
| 4,049,154 | 9/1977 | Burks | 221/76 |
| 4,221,376 | 9/1980 | Handen et al. | 221/154 X |
| 4,267,942 | 5/1981 | Wick, Jr. et al. | 221/2 |
| 4,473,884 | 9/1984 | Behl | 221/3 X |
| 4,504,153 | 3/1985 | Schollmeyer | 221/2 X |
| 4,572,403 | 2/1986 | Benaroya | 221/3 |
| 4,573,606 | 3/1986 | Lewis et al. | 221/3 X |
| 4,607,650 | 8/1986 | Kobayashi et al. | 221/197 X |
| 4,663,621 | 5/1987 | Field et al. | 221/2 X |
| 4,664,289 | 5/1982 | Shimizu et al. | 221/2 |
| 4,695,954 | 9/1987 | Rose et al. | 221/2 X |

Primary Examiner—Charles A. Marmor
Attorney, Agent, or Firm—Kelly, Bauersfeld & Lowry

[57] ABSTRACT

An improved medication dispensing system is provided for controlled preprogrammed dispensing of medication to a patient and for creating a retrievable patient medication record. The system includes a dispensing unit located, for example, at patient bedside within a hospital room or the like and adapted to receive a pair of medication canisters having magazines with individual cassettes which have been preloaded in a preprogrammed manner in the hospital pharmacy or the like respectively to contain scheduled and unscheduled medications for administration to the patient. The dispensing unit is programmed according to individual patient needs to signal a nurse or other personnel at selected times when scheduled medication is prescribed, whereupon the scheduled medication can be accessed for dispensing only after entry of valid nurse or other personnel identification code into a dispensing unit memory. The unscheduled medications may be accessed by the nurse or other personnel in a similar manner but on an untimed basis as required by the patient. The dispensing unit further includes sensors for detecting removal of any medication cassette and for signalling the dispensing unit memory to create a corresponding patient medication record. A data transmission device is provided for selectively programming the dispensing unit memory and/or for reading the patient medication record from the memory.

37 Claims, 7 Drawing Sheets

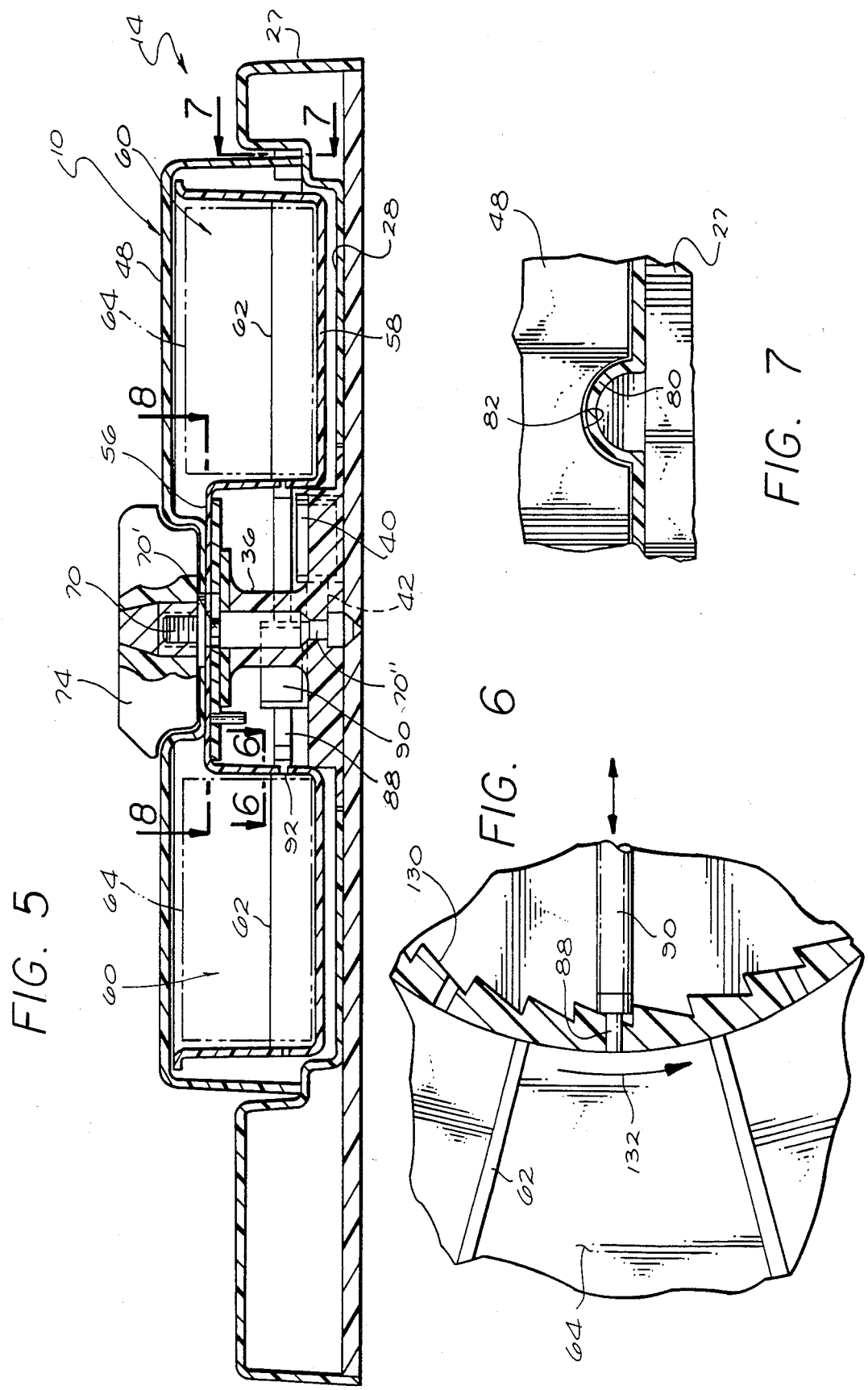

FIG. 8
FIG. 9
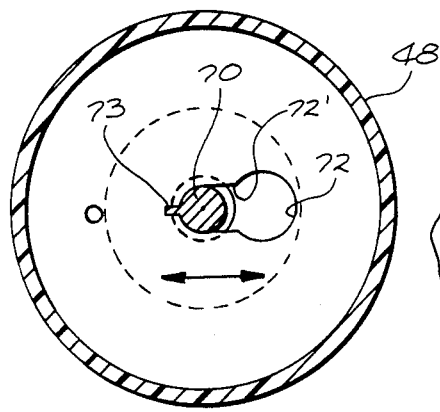
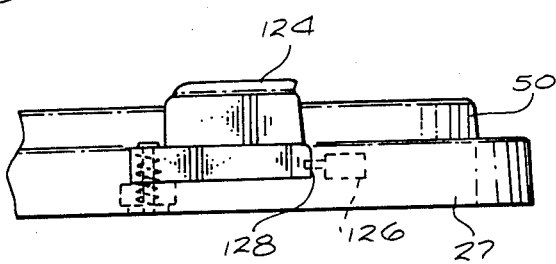
FIG. 10
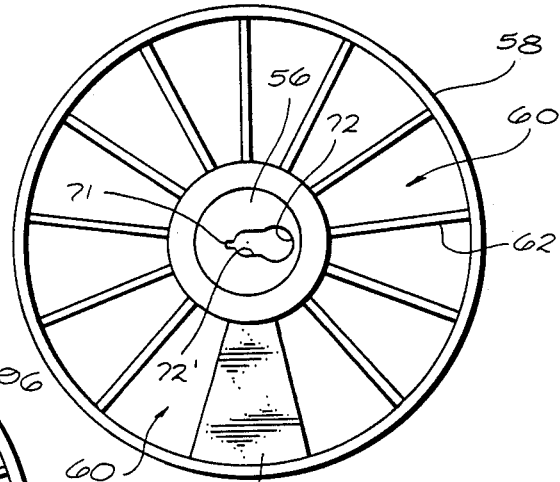
FIG. 11
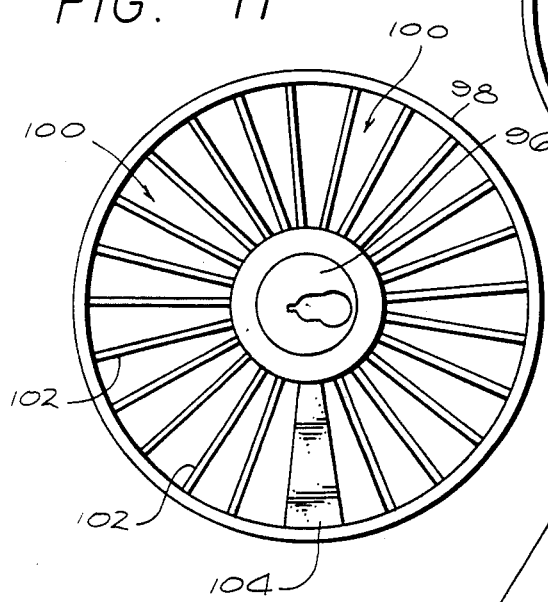
FIG. 14
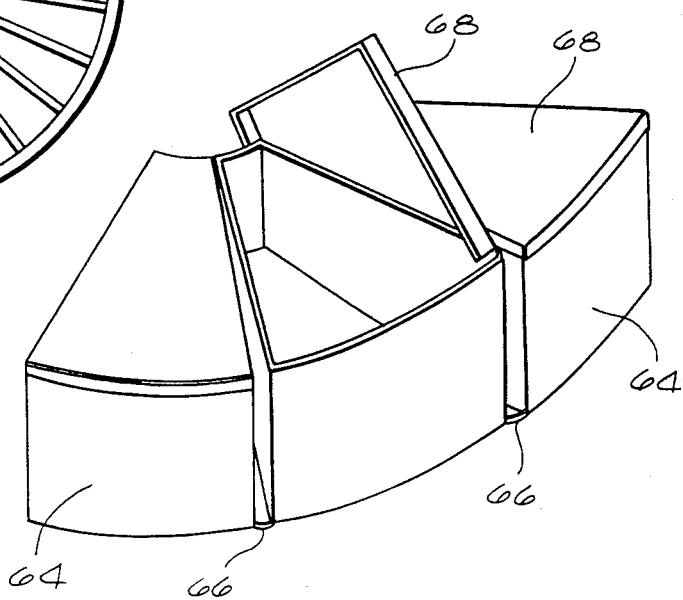

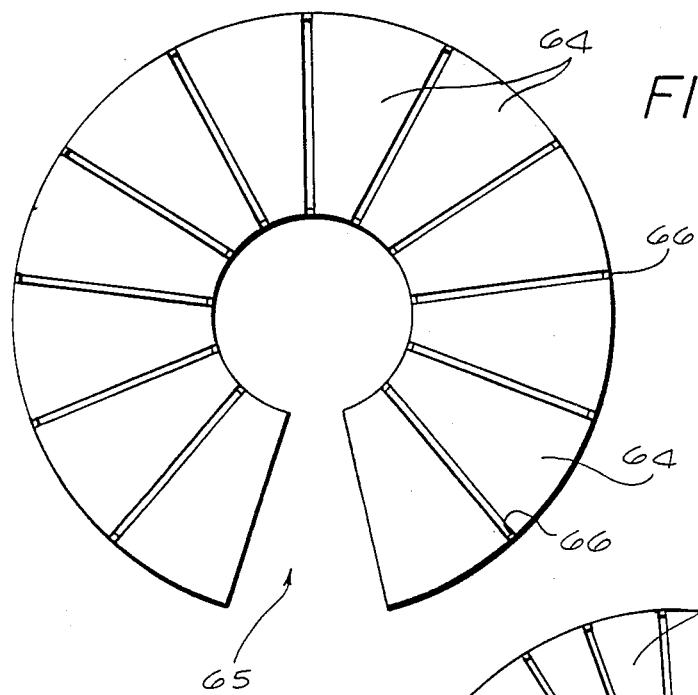
FIG. 12
FIG. 13
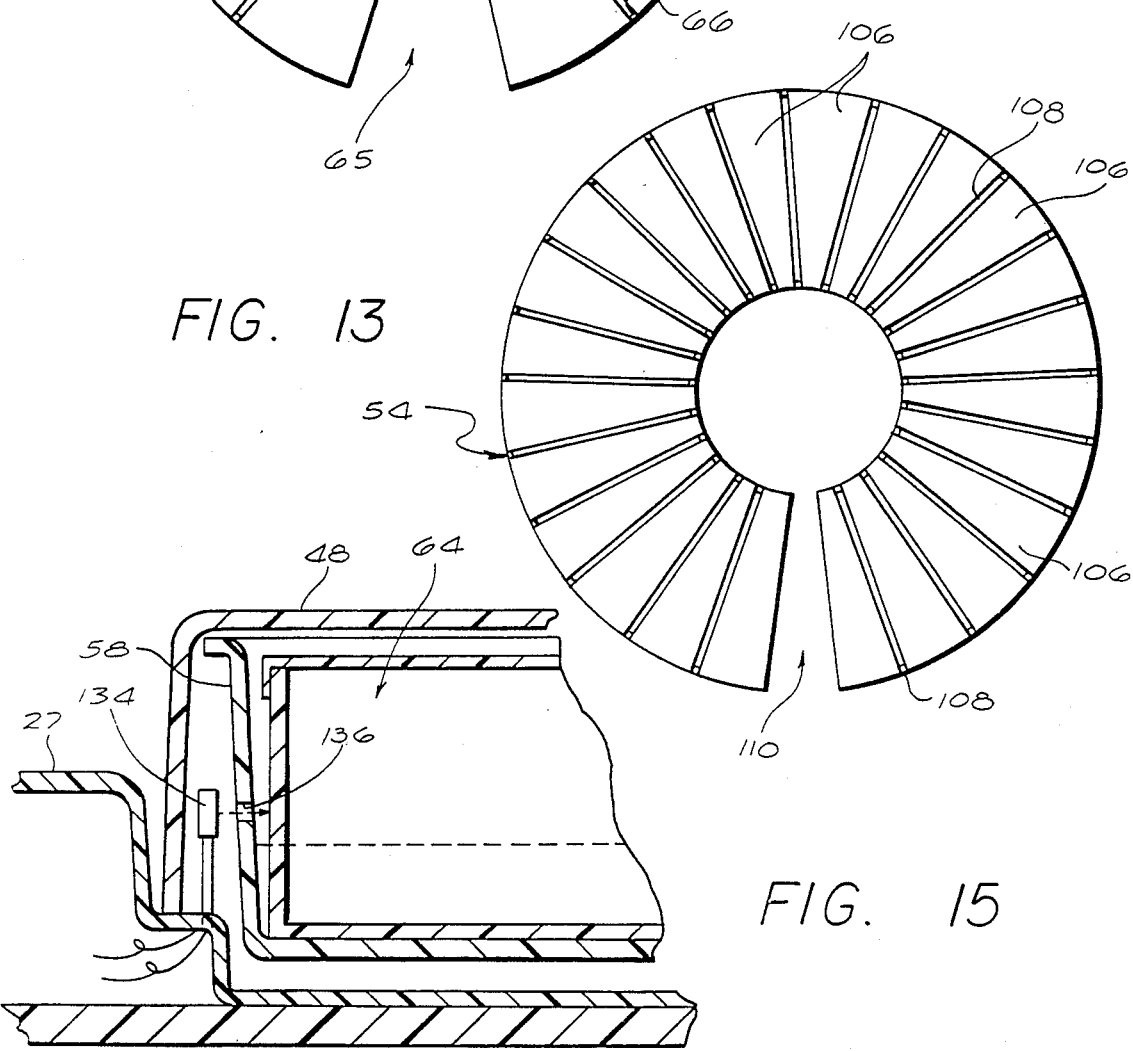
FIG. 15

MEDICATION DISPENSING SYSTEM

BACKGROUND OF THE INVENTION

This invention relates generally to apparatus and methods for controlled dispensing of scheduled and/or unscheduled medications to a hospitalized patient or the like. More specifically, this invention relates to an improved medication dispensing system for controlled medication dispensing in accordance with individually preprogrammed patient requirements and in a manner creating an accurate and detailed patient medication record.

In a hospital environment, patients commonly require administration of a wide range of different medications chosen in accordance with the medical treatment and/or condition of each individual patient. For example, many patients require administration of one or more medications in accordance with scheduled time intervals throughout a given day. Alternately, or in addition, the hospitalized patient may require administration of other medications such as pain relievers, decongestants or the like on an unscheduled, as needed basis. The relative complexities involved in administering many different schedules and unscheduled medications to many different patients increases the potential for human errors such as a failure to deliver the correct medicine and dosage on a timely basis to the correct patient.

More specifically, in the past, patient medications have traditionally been delivered from the pharmacy of a hospital or other medical institution to a centralized paitent floor location for convenient yet limited access by a nurse or other authorized personnel. Written schedules such as nursing and/or patient charts have been provided with appropriate medication information for each patient. The nursing staff has been required to consult these charts for the times and types of medications to be given to each patient, and to manually record each medication dispensing event. Unfortunately, this approach relies almost entirely upon human monitoring of medication schedules and human creation of medication dispensing records. As a result, occasional errors occur in terms of medication timing, type, or dosage, or in the creation of a medication dispensing record.

An improved approach to dispensing of medications in a hospital or the like is described in my previous U.S. Pat. No. 3,762,601, which describes a locked dispensing cabinet positioned, for example, at patient bedside within a hospital room. The dispensing cabinet is loaded periodically by pharmacy personnel and is then locked against direct access by the patient or other unauthorized persons. Timers are set to activate an appropriate nurse signal or alarm when scheduled medication dispensing is due, at which time nursing personnel can unlock the cabinet for access to and administration of the appropriate medication. Accordingly, this dispensing cabinet helps to eliminate dispensing of incorrect medications since the cabinet contains only those medications prescribed for the associated patient. However, when the dispensing cabinet is unlocked, access is permitted to all of the medications loaded therein whereby the medications can still be administered in incorrect dosages and/or removed from the cabinet for administering to the patient at the wrong time. Further, the station does not include automated means for insuring creation of an accurate record of medication administration to a patient.

There exists, therefore, a need for further improvements in medication dispensing apparatus and methods, particularly wherein access to medication is limited to a precise type and limited dosage to be administered to a specific patient, and further, wherein creation of an accurate patient medication record is insured. The present invention fulfills these needs and provides further related advantages.

SUMMARY OF THE INVENTION

In accordance with the invention, an improved medication dispensing system includes a medication dispensing unit located within a hospital patient room or the like, for example, at patient bedside. The dispensing unit is loaded with one or more specific medications for the particular patient, typically including prescribed medications for administration to the patient according to scheduled time intervals as well as one or more medications for administration to the patient on an irregular, as needed basis. In addition, the dispensing unit includes a programmable memory adapted for loading with medication data unique to the patient, wherein this data includes appropriate command information to control dispensing unit operation.

In operation, the medication dispensing unit signals nurse personnel or the like when dispensing of one or more scheduled medications to the patient is timely. Alternatively, nursing personnel may have access to unscheduled medications at any time on an as needed basis by the patient. In either case, medication access is provided until nurse entry of a valid identification code into the dispensing unit memory, after which one or more medications can be accessed and administered to the patient. The dispensing unit includes sensor means for detecting medication removal and for signalling the dispensing unit memory to create therein a patient record indicating medication type and dosage, time of dispensing, and identification of the attending nurse. The patient record can be down-loaded from the dispensing unit memory and transferred to a main records computer for the hospital.

In one preferred form of the invention, the dispensing unit comprises a relatively compact housing mounted or otherwise positioned in a patient room in association with an individual patient. The dispensing unit is adapted for locked reception of a pair of medication canisters which are preloaded by pharmacy personnel or the like and then transported to the patient room for loading into the dispensing unit. Patient data including medication type and dosage identification and dispensing schedule or limitations is entered into the main records computer, for example, at the hospital pharmacy, with appropriate command data being down-loaded to a portable data transmission device which is transported with the canisters to the patient rooom for loading into the dispensing unit.

The dispensing unit, in the preferred form, includes means for locked reception of the medication canisters to prevent unrestricted access to the preloaded medications. One of these medication canisters contains one or more scheduled medications to be administered to the patient in accordance with a physician selected time schedule, whereas the other medication canister carries one or more unscheduled medications for administration to the patient on an as needed basis. The preferred medication canisters each include a rotatable carousel carrying a magazine subdivided into individual cassettes which are rendered accessible one at a time when the canisters are locked into the dispensing unit. The cassettes contain individual dosages of one or more medications, in accordance with patient requirements, and are designed for individual removal from the canisters before the medicines therein can be accessed and dispensed.

In use, when administration of medication to a patient is due or otherwise needed by the patient, a nursing staff member addresses the dispensing unit by keying an appropriate identification code into the dispensing unit memory. In this regard, the dispensing unit includes signal or alarm means for alerting nursing personnel that administration of a scheduled medication is due. Entry of a valid identification code into the dispensing unit memory permits a selected one of the canisters to be accessed by rotation of the carousel of the selected canister to align a medication-containing cassette beneath an open access gate. The sensor means detects cassette removal and thereupon signals the dispensing unit memory to create the patient record which can be read out by the portable data transmission device and subsequently transferred to the main pharmacy computer.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a somewhat diagrammatic perspective view illustrating initial loading of patient medication canisters and entry of correlating patient data into a main records computer of a hospital pharmacy or the like;

FIG. 5 is an enlarged vertical sectional view of the dispensing unit taken generally on the line 5—5 of FIG. 3;

FIG. 6 is an enlarged fragmented horizontal sectional view taken generally on the line 6—6 of FIG. 5;

FIG. 7 is an enlarged fragmented vertical sectional view taken generally on the line 7—7 of FIG. 5;

FIG. 8 is an enlarged fragmented horizontal sectional view taken generally on the line 8—8 of FIG. 5;

FIG. 9 is an enlarged fragmented end elevational view of a portion of the dispensing unit taken generally on the line 9—9 of FIG. 3;

FIG. 10 is a top plan view illustrating a rotatable carousel forming a portion of a preferred scheduled medication canister for the dispensing unit;

FIG. 11 is a top plan view illustrating a rotatable carousel forming a portion of a preferred unscheduled medication canister for the dispensing unit;

FIG. 12 is an enlarged top plan view illustrating a preferred magazine configuration for use with the scheduled medication carousel depicted in FIG. 10;

FIG. 13 is an enlarged top plan view illustrating a preferred magazine configuration for use with the unscheduled medication carousel depicted in FIG. 11;

FIG. 14 is an enlarged fragmented perspective view illustrating preferred construction details for the medication magazine of FIG. 12;

FIG. 15 is an enlarged fragmented vertical sectional view taken generally on the line 15—15 of FIG. 4 and illustrating sensor means for detecting removal of a medication cassette from the scheduled medication magazine;

DETAILED DESCRIPTION OF THE PREFERRED EMBODIMENT

Figure 1:
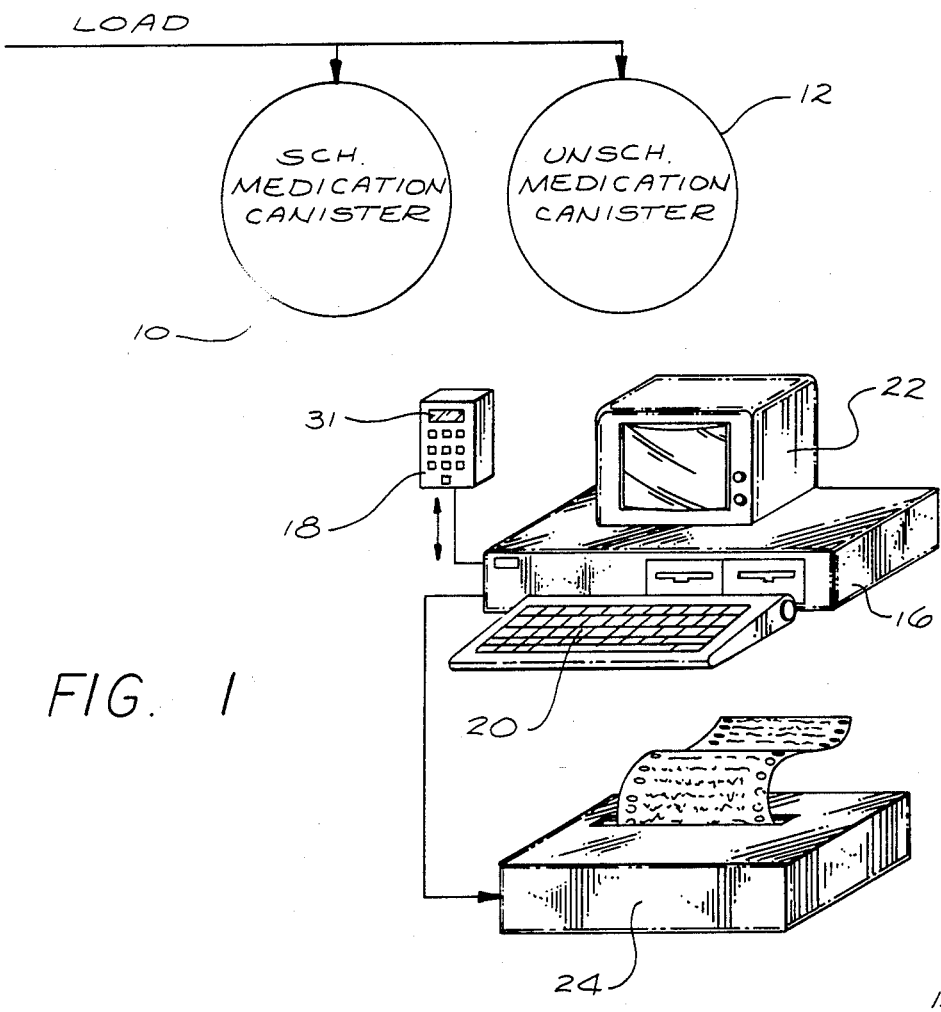
Figure 2:
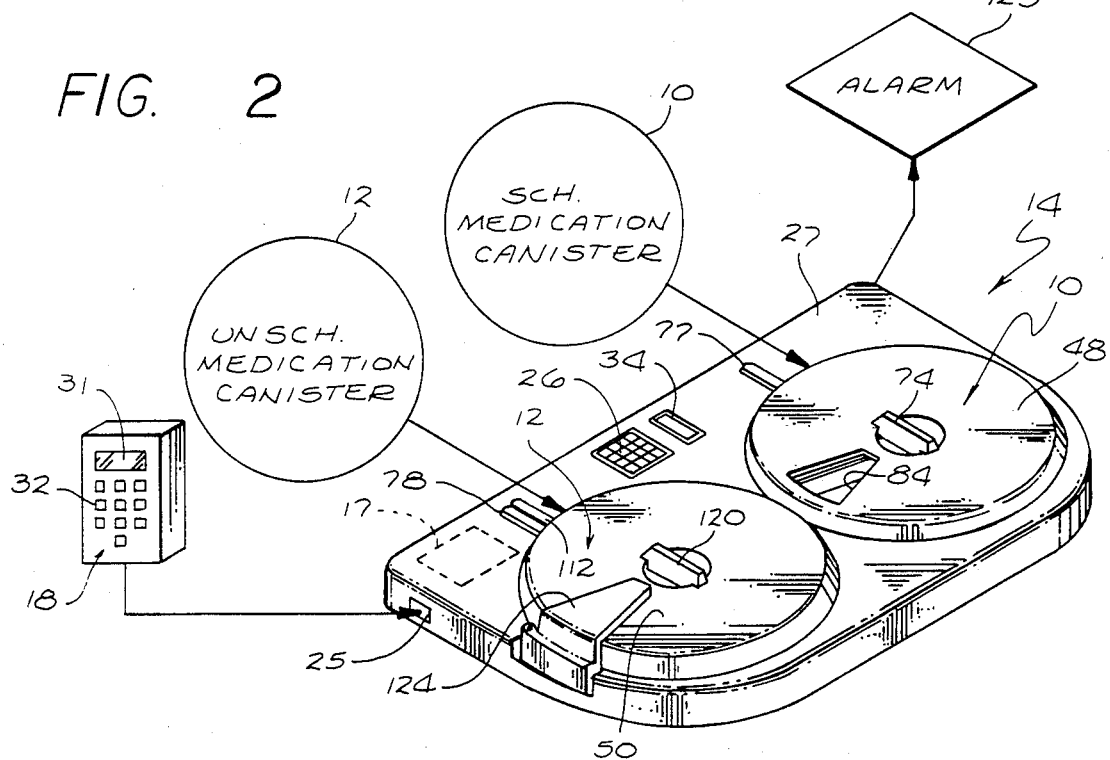
FIG. 2 is a somewhat diagrammatic perspective view illustrating loading of the medication canisters and selected patient data into a medication dispensing unit located, for example, at patient bedside.

An improved medication dispensing system is shown generally in FIGS. 1 an 2 of the exemplary drawings. As shown, the system comprises a pair of portable medication canisters referred to respectively by the reference numerals 10 and 12 and adapted to be loaded with selected medications to be dispensed to an individual patient, for example, in a hospital or the like. The loaded medication canisters 10 and 12 are transported to and locked into a dispensing unit 14 (FIG. 2) located, for example, at patient bedside and including programmable means for restricting access to the medications within the canisters. Program data such as patient identification and information regarding medication type, dispensing schedules, and/or dosages is entered into a main records computer 16, with selected data portions being communicated to an internal dispensing unit memory 17 via a portable data transmission device 18 or the like.

The improved medication dispensing system provides apparatus and methods for controlling access to patient medications in a manner designed to substantially eliminate medication dispensing errors in a hospital environment or the like. More specifically, the improved dispensing system includes the dispensing unit 14 proximally located directly within a patient hospital room at a bedside position or the like for accurate association with the intended patient. The dispensing unit 14 includes means for restricting or limiting access to the medications loaded into the canisters 10 and 12 to authorized hospital personnel such as physicians, nursing staff members or the like, while positively preventing unauthorized access by the patient or other persons. The dipensing unit is adapted to receive the medication canister 10 loaded with selected medications to be administered to the patient in accordance with a specific time schedule, with the second canister 12 being loaded with unscheduled medications for dispensing to the patient on an as needed basis. Signal means are provided for alerting hospital personnel when administration of one or more of the scheduled medications is due. Sensor means are also provided for detecting removal of the scheduled or unscheduled medications from the dispensing unit 14 and for appropriately notifying the dispensing unit memory 17 to create a patient medication record which later can be communicated via the data transmission device 18 to the main records computer 16.

The improved medication dispensing system thus continuously monitors and creates an accurate record of the removal of each and every medication from the dispensing unit for dispensing purposes. The patient medication record for each patient in a hospital can include the dispensing time and type of each medication, the identity of the patient receiving the medication, and the identity of the hospital staff member dispensing the medication. This information will inherently reflect any deviations from the physician-intended medication schedule for each patient and further improves detailed information permitting the cause of any such deviations to be identified. The data transmission device 18 provides a convenient and cost-efficient means for programming a plurality of the dispensing stations 14 with selected patient-unique instructions from the central main records computer 16 and for retreiving the generated patient records for return to the main computer 16.

More particularly, with reference to FIG. 1, the medication dispensing system includes the two medications canisters 10 and 12 which are appropriately loaded with one or more selected medications prescribed for an individual patient in a hospital or the like. The medication canisters 10 and 12 are intended for loading into the hospital pharmacy or the like by appropriate pharmaceutical personnel trained to load the tray with medication types and dosages prescribed by an attending physician. Each of the canisters includes a plurality of individual medication-receiving cassettes (not shown in FIG. 1) for loading with one or more of the medications prescribed for administration to the patient. In the preferred embodiment of the invention, the medication canister 10 is adapted to receive one or more medications to be dispensed in accordance with a prescribed time schedule, such as every two hours, four hours, six hours, etc. with the cassettes being loaded in the sequential order of administration. The second canister 12 is adpated for cassette loading with one or more unscheduled medications such as pain relievers, decongestants, and the like which can be administered to the patient on an as needed basis. These unscheduled medications are preferably loaded into the canister 12 in adjacent groups by medication type.

In accordance with one aspect of the medication dispensing system, detailed patient medication information is entered into the main records computer 16, typically in the hospital pharmacy at the time of loading of the medication canisters. This data typically includes patient identification together with information detailing the medication types, dosages, and schedules according to canister loading. The data is typically entered into the computer 16 via a standard keyboard 20 and may be displayed in a programmed fashion using a standard monitor 22. Alternatively, or in addition, selected data for each patient in the hospital may be printed out as hard copy using any convenient printer 24 associated with the computer 16. Selected portions of this data is down-loaded into the portable data transmission device 18 for subsequent transfer to the dispensing unit 14 at patient bedside, as will be described in more detail. While this data transmission device 18 may take various forms, one preferred construction is exemplified by the hand held memory unit marketed by MSI Data Corporation of Costa Mesa, Calif. under the model designation PDT II. Such device includes convenient means for removable pin-in connection to the main computer 16 or to a jack 25 on one of the dispensing units 14, as viewed respectively in FIGS. 1 and 2. Alternatively, other types of data links can be used such as hard-wired modems and the like to communicate between the main computer 16 and a plurality of the dispensing units 14 located throughout a hospital.

The medication canisters 10 and 12 are transported after loading to the corresponding dispensing unit 14 which has its internal memory 17 preprogrammed with patient identification information. Such preprogramming may occur, for example, by appropriate resetting of the memory and inputting of appropriate information using the data transmission device 18 when a patient is admitted into the hospital. When the unit 14 is then loaded with the medication canisters 10 and 12, the hospital staff member, typically a pharmacy employee such as a medical technician, transports the canisters to the patient room and addresses the dispensing unit memory 17 by entering an appropriate identification code using a standard numeric or alpha-numeric keypad 26 or the like (FIG. 2) located in an accessible position on a unit housing 27. Upon entry of a valid identification code, the dispensing unit memory 17 accommodates locked installation of the medication canisters 10 and 12 respectively into upwardly open chambers 28 and 30 formed in the unit housing 27. The data transmission device 18 (FIGS. 1 and 2), which includes an LCD display 31 or the like and associated keypad 32, is then coupled with the unit memory 17 and appropriately operated for down-loading of selected data into the dispensing unit memory. Such down-loaded data may include, for example, patient identification together with detailed information regarding the types of medications loaded into each canister and the dispensing schedule, if any, associated with each medication. Any errors at this stage are indicated on a dispensing unit LCD display 34 or the like such as by indicating mismatch between the patient associated with the particular dispensing unit and the patient associated with the loaded canisters.

Figure 3:
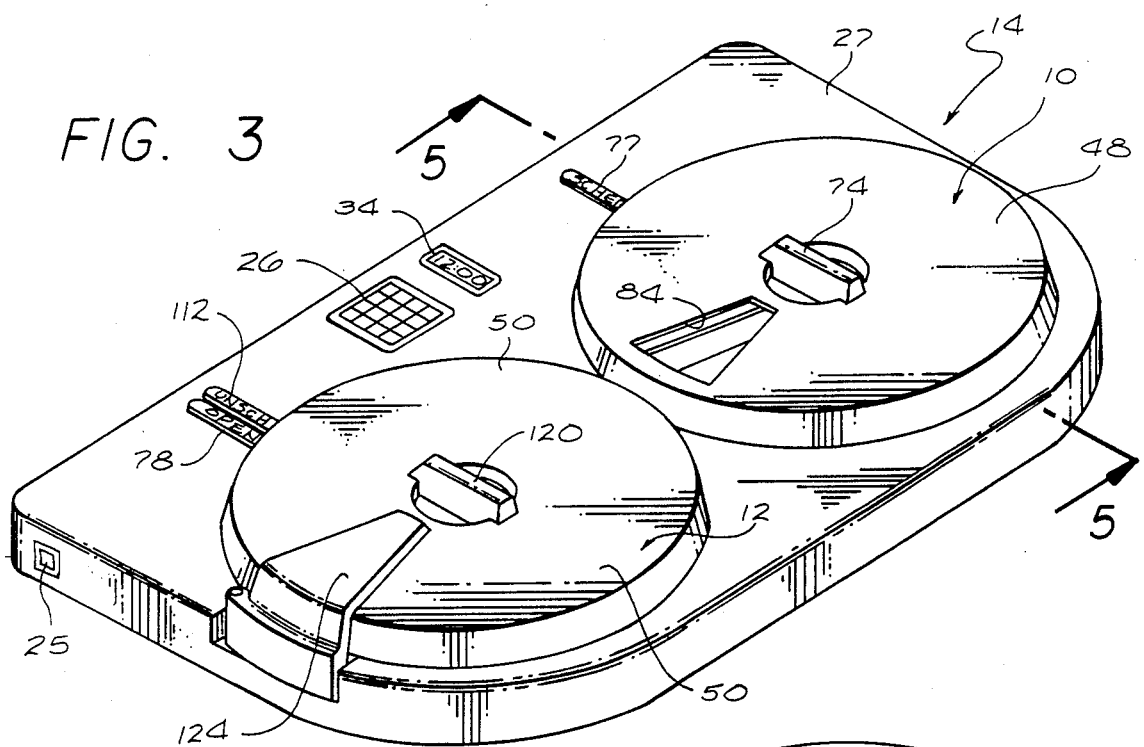
FIG. 3 is an enlarged perspective view illustrating the medication dispensing unit.

The medication dispensing unit 14 is shown in more detail in one preferred form in FIGS. 3–15. More particularly, with general reference to FIGS. 3–5, the exemplary dispensing unit 14 comprises the relatively low profile housing 27 which can be manufactured conveniently from lightweight molded plastic or the like and adapted for facilitated installation within a patient room, for example, by mounting onto the wall or placement onto a table or nightstand at patient bedside. The housing 27 is shaped to include the pair of generally circular and upwardly open chambers 28 and 30 (FIG. 4) for respective locked reception of the medication canisters 10 and 12. The data entry keypad 26 is accessibly positioned at one side of the housing generally adjacent the canister chambers and in close proximity with the display 34. The dispensing unit memory 17 is mounted internally within the housing 27 and comprises any appropriate memory device or devices linked suitably to the keypad 26 and display 34 and adapted for suitable linking to the data transmission device 18 by means of the jack 25 or the like. A portion of the unit memory desirably provides a digital clock which maintains real time and normally displays such time on the unit display 34. Power for the unit 14 can be provided by direct plug-in connection to a standard wall outlet (not shown) or by internal batteries, with a 12 volt dc power supply being preferred.

Figure 4:
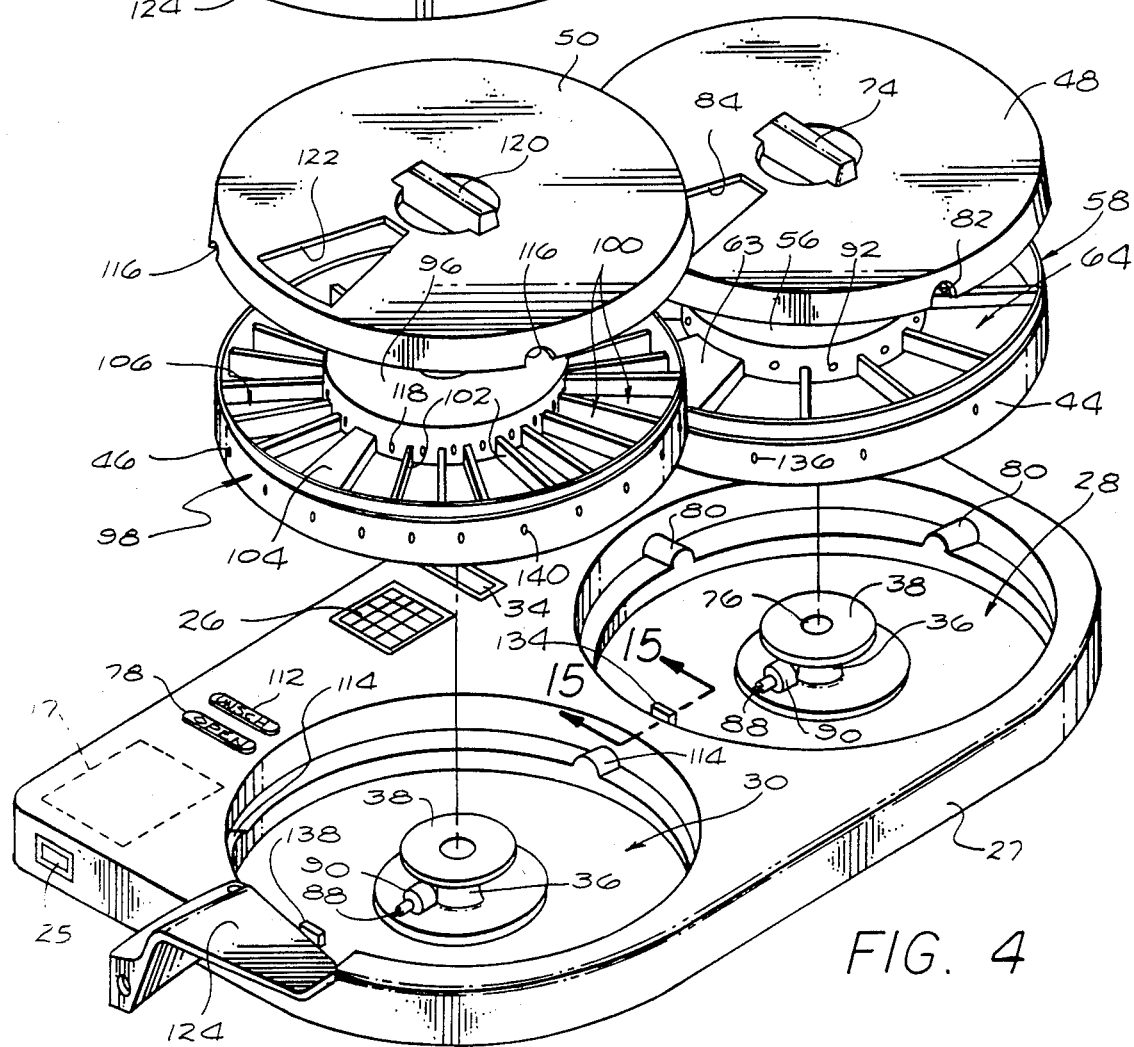
FIG. 4 is an enlarged exploded perspective view illustrating the medication dispensing unit and loading of the medication canisters into the unit.

As shown in FIG. 4, the two canisters 10 and 12 have a generally circular size and shape for reception into the housing chambers 28 and 30, respectively. In this regard, each of the housing chambers 28 and 30 includes a central upstanding pedestal 36 having an upper circular plate 38 upon which the associated canister is rotatably supported. A locking solenoid assembly 40 shown in FIG. 5 is positioned beneath the support plate 38 of each pedestal 36 and includes a radially inwardly directed plunger 42 for locking engagement with the associated canister, as will be described in more detail.

Each of the canisters 10 and 12 comprises a generally circular lower carousel 44 and 46, respectively, in combination with a corresponding pair of generally circular canister covers 48 and 50. These carousel and cover combinations 44, 48 and 46, 50 are designed for respective reception and enclosure of a pair of generally annular medication magazines 52 and 54 (FIGS. 11 and 12) for receiving the medications to be dispensed ultimately to the patient.

More specifically, with particular reference to the scheduled medication canister 10, the associated lower carousel 44 comprises a generally circular center plate 56 sized to seat upon the pedestal support plate 38 within the associated housing chamber 28. The center carousel plate 56 is joined at its outer periphery to a dished, generally annular outer tray 58 as viewed best in FIGS. 5 and 10. This outer tray 58 is subdivided into a radially arranged array of generally pie-shaped receptacles 60 each separated from the adjacent receptacle by a radially extending divider wall 62 of relatively low height. Importantly, the array of receptacles 60 is interrupted by a blank 63 defined by a platform bridging the tops of two adjacent divider walls 62 to eliminate the receptacle between these specific divider walls at one position about the periphery of the carousel 44. In the illustrative drawings, the scheduled medication carousel 44 is shown to include a plurality of twelve receptacles 60 together with the single blank 63, thereby providing for up to twelve scheduled medication dispensing events, for example, every two hours, during a 24-hour period.

The scheduled medication carousel 44 is adapted to receive the medication magazine 52, as shown best in FIGS. 12 and 14. This magazine 52 is conveniently formed from a lightweight plastic which can be blow or vacuum molded to include a plurality of generally pie-shaped cassettes 64 arranged in a generally annular configuration. The number of such cassettes 64 and their sizes and shapes are chosen for individual seating within the receptacles 60 of the carousel 44. In this regard, one adjacent pair of the cassettes 64 is separated by a gap 65 to correspond with the tray blank 63. In addition, the lower margins of adjacent cassettes 64 are slightly spaced by thin, fragile membranes 66 which are split apart by the tray divider walls 62 upon cassette seating into the tray 58. Simple hinged lids 68 are further provided to close the cassettes.

At the hospital pharmacy, the magazine 52 is loaded into the carousel 44 in a manner splitting the membranes 66 to separate the cassettes. The individual cassettes 64 are loaded in sequence with the appropriate medication or medications for the selected patient, after which the cassette lids 68 are closed, conveniently with a snap action. The carousel 44 and magazine 52 are then covered by the canister cover 48 which includes a central, downwardly extending spindle 70. The spindle 70 fits downwardly through an offset enlarged portion of an opening 72 formed in the carousel center plate 56, and the carousel is then shifted laterally for receiving a narrower diameter, upper grooved region 70' of the spindle into a centered, narrower portion 72' of the plate opening 72, thereby locking the cover 48 and carousel 44 together as a unit with the loaded magazine 52 therein. An outwardly radiating key 73 on the spindle 70 seats within a drive recess 71 in the carousel plate 56 for rotational driving engagement between the spindle and carousel, with an accessible handle 74 at the upper end of the spindle being manually rotatable to rotate the carousel beneath the canister cover 48.

The loaded and assembled scheduled medication canister 10, as described, is placed into the chamber 28 of the dispensing unit 14 by seating the spindle 70 into an upwardly open central bore 76 formed in the chamber pedestal 36. In this regard, entry of a valid pharmacy technician identification code into the unit memory 17, followed by depression of a scheduled medication pushbutton 77 to select the scheduled medication canister 10 and depression of a separate pushbutton 78 marked "open" is effective to briefly retract the spring-loaded plunger 42 of the associated solenoid locking assembly 40 to permit removal of a previous canister 10. The fresh loaded canister 10 may then be installed with a pointed lower end of the spindle 70 (FIG. 5) forcing the plunger 42 to retract, followed by plunger return to lock into a lower spindle groove 70''. The upper handle 74 on the cover 48 facilitates canister manipulation during this procedure. An arrangement of upstanding protrusions 80 at the periphery of the chamber 28 registers with mating recesses 82 at the periphery of the cover 48 to insure canister installation in a single predetermined position within the canister. In this position, the magazine blank 63 is positioned beneath an open access gate 84 in the cover 48 to deny access to any of the medication cassettes. Rotation of the magazine 52 beneath the nonrotating cover 48 to any alternative rotational position is initially prevented by the spring-loaded plunger 88 of an index solenoid assembly 90, wherein this plunger 88 is initially advanced to a receptor hole 92 in the tray hub at the inboard side of the carousel tray 58.

The second canister 12 associated with unscheduled patient medications is similarly constructed and adapted for locked reception into the second chamber 30 within the dispensing unit 14. More particularly, with reference to FIGS. 4, 11 and 13, the second canister 12 includes the lower carousel 46 of generally circular configuration to include a circular center support plate 96 joined to a surrounding dished annular tray 98. This outer tray 98 is also subdivided into an annular array of generally pie-shaped receptacles 100 which may differ in number from the scheduled medication canister 10, with 24 such receptacles 100 separated by short divider walls 102 being depicted in the illustrative drawings. Once again, a raised platform may be provided between two of the receptacles 100 to define a blank 104 to insure proper initial installation of the associated medication-containing magazine 54, as will be described.

The magazine 54 for the second canister 12 is formed in a manner similar to the previously described magazine 52 to include a lightweight annular array of shallow cassettes 106 joined at adjacent bases by breakable membranes 108. In addition, at one side, the cassette array includes a narrow gap 110 corresponding with the blank 104 of the tray 98. The cassettes 106 can thus be loaded in one orientation into the tray 98, whereupon the membranes 108 are fractured to separate the cassettes 106 from each other. The cassettes 106 may further include snap closure lids or the like, similar to the previously described cassettes 64, (FIG. 14) although such lids are not shown in the illustrative drawings.

After the cassettes 106 are installed into the tray 94, they are loaded with selected unscheduled medications to be administered to the patient on an as needed basis. For example, selected cassettes may be loaded with aspirin, other cassettes may be loaded with stronger pain relivers, and still other cassettes may be loaded with other medications as appropriate for the patient. The medications are normally loaded into the cassettes in adjacent groups by medicine type, with the specific order and manner of cassette loading being inputted to the main computer 16 (FIG. 1) for subsequent transfer via the data transmission device 18 to the memory 17 of the individual medication dispensing unit 14.

When the magazine 54 is loaded with the desired unscheduled medications, the associated canister cover 50 is locked over the carousel 46 preferably using a depending spindle (not shown) of the type described with respect to the scheduled medication canister 10. The thus-assembled canister 12 can then also be transported to the patient room for installation into the dispensing unit 14 by appropriate locking of the spindle with the chamber pedestal 36 (FIG. 4). Such locking of the canister 12 within the chamber 30 is accomplished in the same manner as described with respect to the scheduled medication canister 10, namely, by the pharmacy technician entering a valid access code into the unit memory 17 together with depression of unscheduled medication pushbutton 112 and the "open" button 78. This action causes the locking solenoid plunger 42 of the associated solenoid assembly 40 to retract and permit removal of a previous canister followed by locked installation of the freshly loaded canister 12. Upstanding protrusions 114 formed within the periphery of the unit chamber 30 mesh with associated recesses 116 in the periphery of the cover 50 to insure canister installation into the chamber 30 in a single, predetermined rotational position. Conveniently, the arrangement of protrusions 114 and recesses 116 associated with the unscheduled medication canister 12 will differ from the arrangement of protrusions 80 and recesses 82 associated with the scheduled medication canister 10 to prevent inadvertent installation of the canisters 10 and 12 into the wrong unit chambers.

In the preferred form, the lower carousel 46 and medication magazine 54 of the unscheduled medication canister 12 are supported within the unit chamber 30 for rotation beneath the cover 50. Such rotation is initially prevented by an index solenoid assembly 90 of the type shown and described with respect to FIGS. 5 and 6, wherein this solenoid assembly for the chamber 30 has a spring-loaded plunger locked into a receptor hole 118 at the top inboard side of the tray blank 104. However, when this plunger is retracted from the receptor hole 118, the carousel 46 can be freely rotated beneath the cover 50 by manual rotation of a handle 120 secured in an accessible position at the upper end of the spindle. Such rotation of the carousel 46 is effective to displace the medication-containing cassettes 106 beneath a generally pie-shaped open access gate 122 formed in the canister cover 50. This access gate 122 is normally closed by a door 124 swingably mounted onto the dispensing unit 14 and spring loaded, as viewed in FIGS. 4 and 10, to pivot toward an open position. A release solenoid assembly 126 includes a spring-loaded plunger 128 for releasably locking the door 124 in a position closing the access gate 122 (FIG. 10).

After both medication canisters 10 and 12 have been installed into the dispensing unit 14 located at patient bedside, the dipsensing unit memory 17 controls operation of the unit 14 to insure limited access to the medications stored within the unit. More specifically, with respect to scheduled medications, the unit memory 17 responds to inputted data unique to the particular patient and the medications loaded within the canister 10 to prevent access to the scheduled medications except within limited window time frames during which dispensing of the medications to the patient is timely. For example, when dispensing of scheduled medication is due, the unit 17 memory signals an appropriate audio or visual alarm 129 (FIG. 2) such as a nurse call button or the like to indicate to the nursing staff that medication is due for dispensing to a particular patient. When this signal occurs, the memory 17 will permit limited nursing staff access to the next scheduled medication cassette 64 in sequence within a limited window time frame, such as about fifteen to thirty minutes as may be preprogrammed into the unit memory.

When the scheduled medication signal occurs, the unit memory 17 is programmed to require entry of a nurse or hospital staff identification code using the unit keypad 26. The unit display 34 appropriately indicates entry of a valid identification code to permit the staff member to select the scheduled medication canister 10 by manual depression of the pushbutton 77 on the unit housing 27. Nurse access to the medication is limited, however, in that the memory 17 can be preprogrammed to distinguish a nurse identification code from a pharmacy technician code, and to permit removal of either canister only when a proper technician code is entered. Depression of the scheduled medication pushbutton 77 operates the index solenoid assembly 90 to retract the plunger 88 thereof from the receptor hole 92 associated initially with magazine blank 63. This retracts the plunger 88 into association with a one-way ratchet surface 130 on the inboard side of the associated tray hub to permit unidirectional rotation of the carousel 44 as indicated by arrow 132 in FIG. 6. Such rotation of the carousel 44 is accomplished easily by manual grasping and rotation of the upper handle 74. Importantly, the solenoid plunger 88 is retracted sufficiently and momentarily to clear the teeth of the ratchet surface 130, but the plunger 88 is spring-loaded to return to an advanced position for reception into the next receptor hole 92 in sequence. The next receptor hole 92 is aligned with the plunger 88 when the next cassette 64 in sequence is rotated to a position aligned beneath the open access gate 84 in the cover 48. Accordingly, the solenoid assembly 90 and its plunger 88 permit tray rotation unidirectionally to the next cassette position whereupon the carousel 44 is relocked against further rotation.

The cassette 64 rotated beneath the cover access gate 84 is now exposed for manual access and removal from the carousel 44. Such removal is detected by a sensor 134 which may be located at the outer periphery of the chamber 28, as viewed in FIG. 15. In one form, this sensor 134 may comprise an optical detector for viewing through an aligned port 136 in the carousel 44 for detecting removal of the cassette 64 associated with that port 136. When cassette removal is detected, the sensor 134 appropriately signals the unit memory 17 which correlates the cassette removal event with the rotational position of the carousel 44 to create a patient medication dispensing record including, for example, patient identification, time and date, types and doses of medications dispensed, and the staff member responsible for medication dispensing.

After the cassette 64 is removed from the carousel 44, the cassette may be opened quickly and easily to access the medications therein. These medications can thus be administered to the patient and the cassette 64 discarded. Importantly, additional medications within the scheduled medication canister 10 are locked against access until the next preprogrammed dispensing time occurs.

Unscheduled medications within the canister 12 may be accessed at any time by appropriate input of a valid nurse or staff member identification code into the dispensing unit memory 17, by means of the unit keypad 26. When such valid code is entered, depression of the unscheduled medicaton pushbutton 112 will retract the plunger of the associated indexing solenoid assembly to permit rotation of the associated carousel 46 within the chamber 30. Such rotation is also desirably unidirectional by virtue of an interior ratchet surface on the carousel tray 98, similar to that described with respect to the scheduled medication tray 58. However, with the unscheduled medication canister, the indexing solenoid plunger desirably remains retracted until subsequent depression of pushbutton 112 to permit continued carousel rotation to the selected rotational position. An appropriate sensor 138 (FIG. 4) is provided to detect the rotational position of the carousel, for example, by counting peripheral ports 140, with the unit LCD display responding thereto by indicating the medication rotated to a position beneath the cover access gate 122.

When the desired unscheduled medication-containing cassette 106 is located beneath the access gate 122 the "open" pushbutton 78 can be depressed to operate the release solenoid assembly 126 for retracting its plunger 128 form the door 124. This permits the spring-loaded door to swing to the open position as viewed in FIG. 4 for manual access to the underlying medication-containing cassette 106. The particular cassette 106 can thus be removed and the medication therein dispensed to the patient, with the associated sensor 138 also detecting cassette removal for appropriate signalling of the unit memory 17 to create the desired patient medication dispensing record. The door 124 can then be pivoted back to the closed position for relocked engagement with the plunger of the release solenoid assembly 126 thereby denying access to the unscheduled medications until reentry of a valid staff member identification code into the unit memory.

At the conclusion of a medication dispensing cycle, for example, at the end of a 24-hour period, the canisters 10 and 12 can be retrieved by appropriate pharmacy personnel or the like and replaced by freshly loaded canisters containing medications chosen for the needs of the particular patient. At this time, the portable data transmission device 18 can be used to revise the medication identificaiton and/or scheduling information programmed into the unit memory 17. In addition, the data transmission device 18 can be used to down-load the patient medication dispensing record from the unit memory 17 for transfer subsequently to and un-loading into the main records computer 16. Medication dispensing records for all patients can thus be stored within the main records computer 16 and appropriately printed out, as desired, using the printer 28 (FIG. 1).

Figure 16:
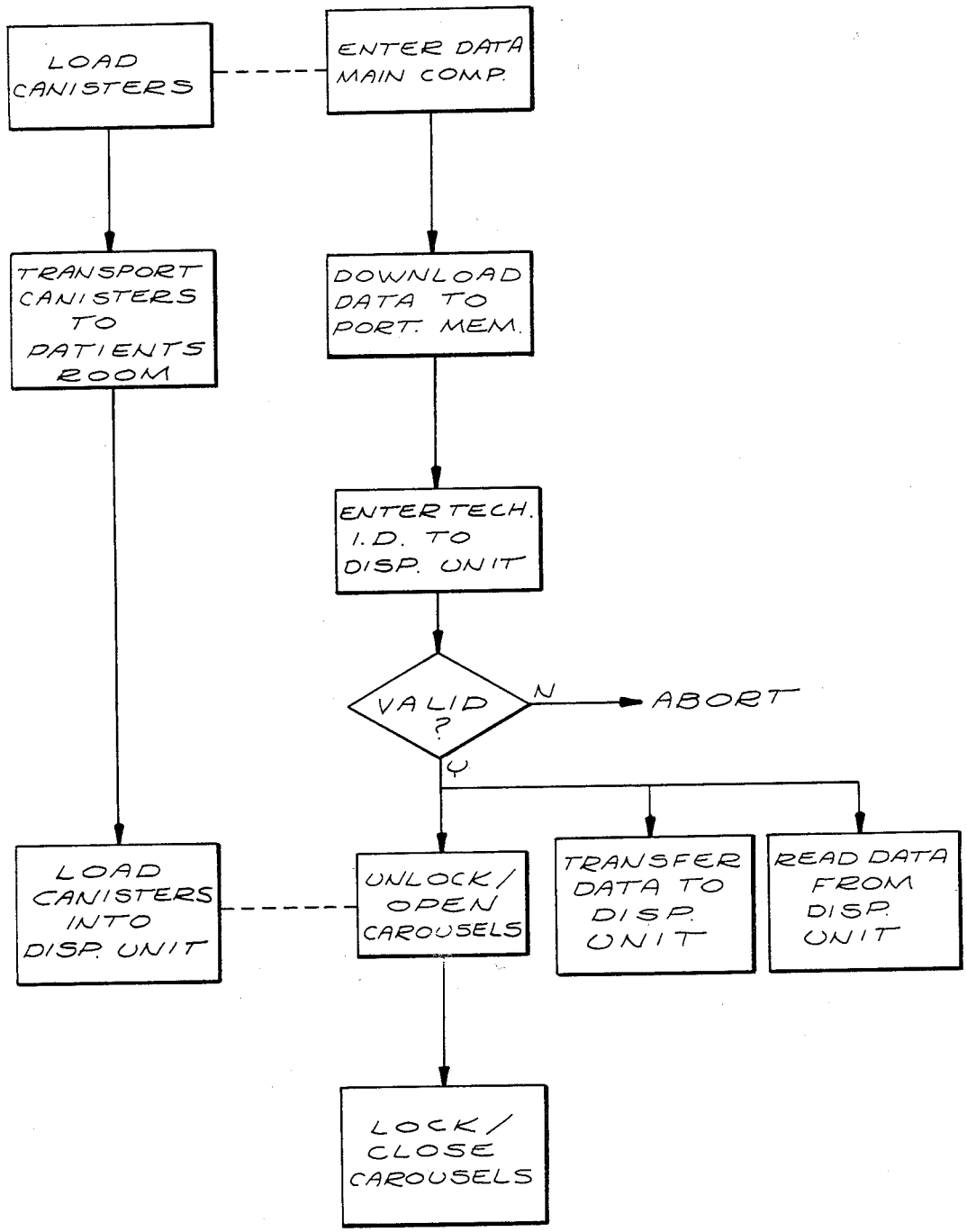
FIG. 16 is a schematic flow diagram depicting processing and data steps for loading and locking the medication canisters into the dispensing unit.
Figure 17:
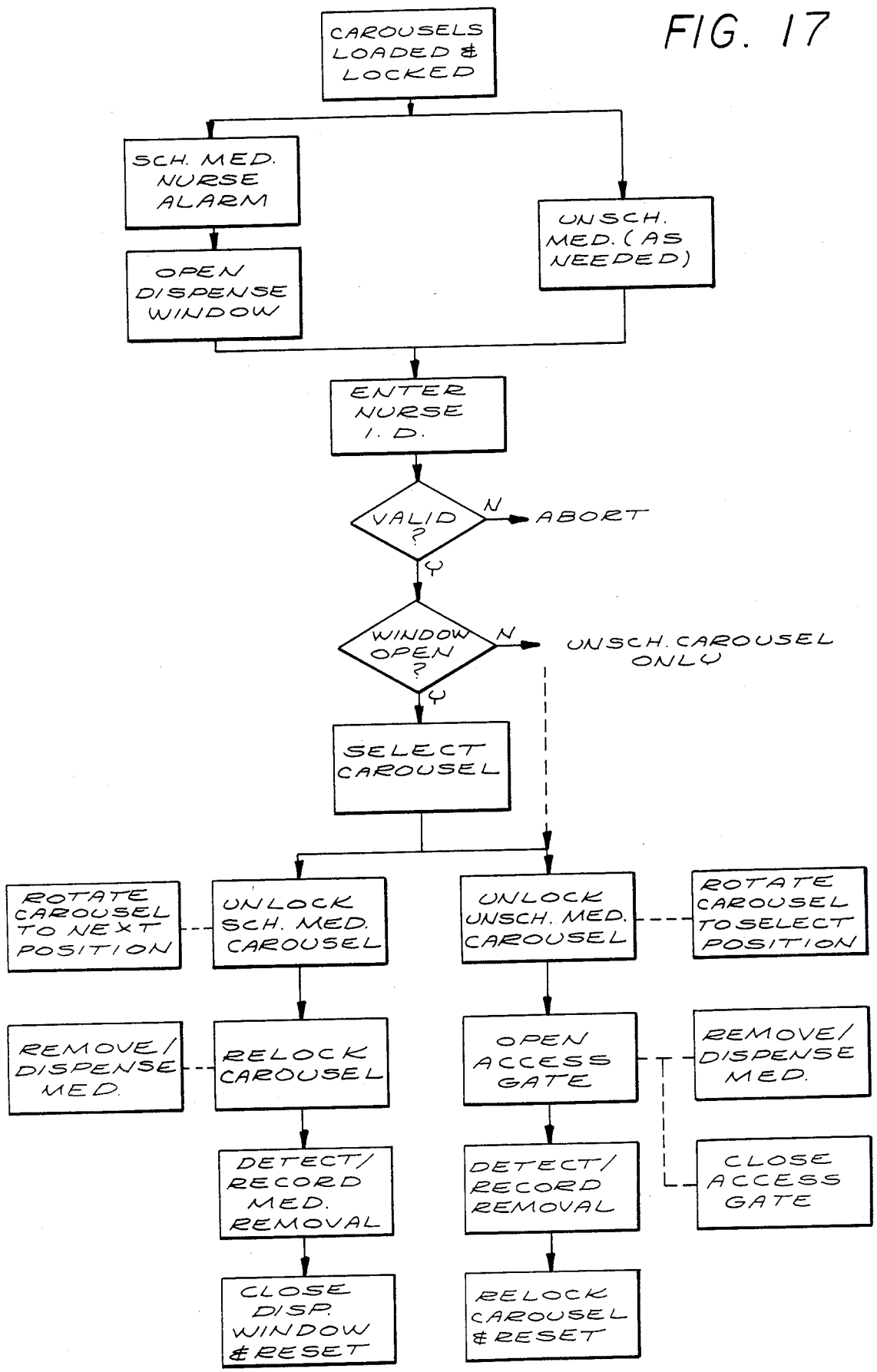
FIG. 17 is a schematic flow diagram depicting operation of the dispensing unit for selecting and dispensing patient medications.

The general programmed operation of the medication dispensing system of the present invention is summarized in the block diagrams shown in FIGS. 16 and 17.

More particularly, with reference to FIG. 16, the medication canisters 10 and 12 are loaded at a centralized location such as in a hospital pharmacy or the like and appropriate data is entered into the main records computer 16. Portions of this data are down-loaded to the portable data transmission device which is transported along with the loaded canisters to the dispensing unit 14 in the patient room. At this juncture, the transporting technician addresses the dispensing unit 14 by entering the appropriate code into the dispensing unit memory. In the absence of entry of valid identification, the dispensing unit denies access to the technician.

Upon entry of a valid identification code, the transporting technician can unlock and remove any canisters within the dispensing unit and replace them with the freshly loaded canisters containing patient medications. At the same time, the technician up-loads the appropriate program and related control data to the dispensing unit while reading the patient medication record which may exist within the unit memory. The loaded canisters are locked in place to permit medication dispensing under the restrictions imposed by the unit memory.

As shown in FIGS. 17, the programmed memory activates an alarm or signal when dispensing of scheduled medications is due and thereupon opens a limited time dispensing window during which scheduled medications may be accessed. Unscheduled medications may be accessed at any time on an as needed basis. In either case, to access the medication, the nurse or other appropriate personnel is required to address the dispensing unit by entry of a valid identification code.

When a valid nurse code is entered into the unit, the scheduled or unscheduled medication canisters 10 or 12 are selected by depression of the pushbutton associated therewith. This permits the selected carousel 44 or 46 to be rotated to transport a loaded medication cassette 64 or 106 to a position beneath the associated access gate. A scheduled medication cassette 64 can then be removed directly, whereas the "open" pushbutton 78 must be depressed to open the door 124 before an unscheduled medication cassette 106 can be removed. In either case, cassette removal is detected by the related sensor to create the appropriate dispensing record for the particular patient. The scheduled medication carousel 44 remains locked against further rotation until the next dispensing time occurs, whereas the cover plate 50 for the unscheduled medication carousel 46 may be rotated to selected additional unscheduled medications until the door 124 is returned to the closed position.

The medication dispensing system of the present invention thus provides apparatus and method for close and accurate control over dispensing of medications to patients in a hospital or the like. The system automatically restricts medication access to authorized personnel while placing and storing appropriate medications in close proximity with the intended patient. When medications are dispensed, a thorough and accurate dispensing record is automatically created.

A variety of modifications and improvements to the improved medication dispensing system described herein will be apparent to those skilled in the art. Accordingly, no limitation on the invention is intended by way of the description and drawings, except as set forth in the appended claims

What is claimed is:

1. A medication dispensing system, comprising:
   a first medication canister for receiving at least one scheduled medication for administration to a patient in accordance with a prescribed time schedule;

a second medication canister for receiving at least one unscheduled medication for administration to the patient on an as needed basis;

a dispensing unit for individual association with the patient and including housing means for locked reception of said first and second canisters to prevent unauthorized removal of said canisters from said unit;

first accesss means for restricting access to the at least one scheduled medication within said first canister to authorized personnel and further to predetermined medication doses during time windows of selected duration at intervals in accordance with said prescribed time schedule;

second access means for restricting access to at least one unscheduled medication within said second canister to said authorized personnel on an as needed basis by the patient; and means for detecting removal of medications from said first and second canisters and for creating a record thereof;

said first canister including a plurality of cassettes containing said at least one scheduled medication, said first access means restricting access to said cassettes for removal from said first canister one at a time by said authorized personnel, and said detecting means sensing such cassette removal.

2. The medication dispensing system of claim 1 wherein said detecting and record-creating means comprises sensing means for sensing removal of medications from said first and second canisters, and memory means signalled by said sensing means upon such removal of medications from said canisters, said memory means being programmable for responding to such signalling by said sensing means to create said record.

3. The medication dispensing system of claim 1 including a plurality of said dispensing units each associated with a respective one of a plurality of patients, and a plurality of sets of said first and second canisters, each of said sets being associated individually with a respective one of said dispensing units.

4. The medication dispensing system of claim 3 further including means for retrieving the record of removal of medications from each of said dispensing units.

5. The medication dispensing system of claim 4 further including a main records computer, said retrieving means being for transferring each of said retrieved records to said main records computer.

6. A medication dispensing system, comprising:
a first medication canister for receiving at least one scheduled medication for administration to a patient in accordance with a prescribed time schedule;

a second medication canister for receiving at least one unscheduled medication for administration to the patient on an as needed basis;

a dispensing unit for individual association with the patient and including housing means for locked reception of said first and second canisters to prevent unauthorized removal of said canisters from said unit;

first access means for restricting access to the at least one scheduled medication within said first canister to authorized personnel and further to predetermined medication doses during time windows of selected duration at intervals in accordance with said prescribed time schedule;

second access means for restricting access to at least one unscheduled medication within said second canister to said authorized personnel on an as needed basis by the patient; and means for detecting removal of medications from said first and second canisters and for creating a record thereof;

said second canister including a plurality of cassettes containing said at least one unscheduled medication, said second access means restricting access to said cassettes for removal from said second canisters one at a time by said authorized personnel, and said detecting means sensing such cassette removal.

7. A medication dispensing system, comprising:
a first medication canister for receiving at least one scheduled medication for administration to a patient in accordance with a prescribed time schedule;

a second medication canister for receiving at least one unscheduled medication for administration to the patient on an as needed basis;

a dispensing unit for individual association with the patient and including housing means for locked reception of said first and second canisters to prevent unauthorized removal of said canisters from said unit;

first access means for restricting access to the at least one scheduled medication within said first canister to authorized personnel and further to prescribed medication doses during time windows of selected duration at intervals in accordance with said prescribed time schedule;

second access means for restricting acess to at least one unscheduled medication within said second canister to said authorized personnel on an as needed basis by the patient; and means for detecting removal of medications from said first and second canisters and for creating a record thereof;

said first canister comprising a generally circular carousel including a general annular tray, a generally annular magazine defining a plurality of medication-receiving cassettes for seated reception upon said tray, a canister cover for releasable locked engagement with said carousel in overlying relation with said magazine and having an access opening formed therein for exposing one of said cassettes, and handle means at the upper side of said cover and coupled to said carousel for manual rotation of said carousel upon manual rotation of said handle means.

8. The medication dispensing system of claim 7 wherein said dispensing unit includes means for releasable locked engagement with said first canister.

9. The medication dispensing system of claim 7 wherein said dispensing unit includes means for locking said carousel against rotation when said first canister is locked into said dispensing unit, said locking means being releasable to permit unidirectional rotation of said carousel to rotate the next cassette in sequence to a position beneath said access opening and for thereupon relocking to prevent further rotation of said carousel.

10. The medication dispensing system of claim 9 wherein said first access means includes code entry means, and memory means for recognizing a predetermined code entered into said entry means and for thereupon releasing said locking means to permit said unidirectional rotation of said carousel.

11. A medication dispensing system, comprising:
a first medication canister for receiving at least one scheduled medication for administration to a patient in accordance with a prescribed time schedule;
a second medication canister for receiving at least one unscheduled medication for administration to the patient on an as needed basis;
a dispensing unit for individual association with the patient and including housing means for locked reception of said first and second canisters to prevent unauthorized removal of said canisters from said unit;
first access means for restricting access to the at least one scheduled medication within said first canister to authorized personnel and further to predetermined medication doses during time windows of selected duration at intervals in accordance with said prescribed time schedule;
second access means for restricting access to at least one unscheduled medication within said second canister to said authorized personnel on an as needed basis by the patient; and
means for detecting removal of medications from said first and second canisters and for creating a record thereof;
said second canister comprising a generally circular carousel including a general annular tray, a generally annular magazine defining a plurality of medication-receiving cassettes for seated reception upon said tray, a canister cover for releasable locked engagement with said carousel in overlying relation with said magazine and having an access opening formed therein for exposing one of said cassettes, and handle means at the upper side of said cover and coupled to said carousel for manual rotation of said carousel upon manual rotation of said handle means.

12. The medication dispensing system of claim 11 wherein said dispensing unit includes means for releasable locked engagement with said second canister.

13. The medication dispensing system of claim 11 wherein said dispensing unit includes means for locking said carousel against rotation when said second canister is received therein, said locking means being releasable to permit unidirectional rotation of said carousel.

14. The medication dispensing unit of claim 13 wherein said second access means includes code entry means, and memory means for recognizing a predetermined code entered into said entry means and for thereupon releasing said locking means to permit said unidirectional rotation of said carousel.

15. A medication dispensing system, comprising:
a first medication canister for receiving at least one scheduled medication for administration to a patient in accordance with a prescribed time schedule;
a second medication canister for receiving at least one unscheduled medication for administration to the patient on an as needed basis;
a dispensing unit for individual association with the patient and including housing means for locked reception of said first and second canisters to prevent unauthorized removal of said canisters from said unit; and
access means for restricting access to the at least one scheduled medication within said first canister to authorized personnel and further to predetermined medication doses during time windows of selected duration at intervals in accordance with said prescribed time schedule; and
said access means further restricting access to the at least one unscheduled medication within said second canister to said authorized personnel on an as needed basis by the patient.

16. The medication dispensing system of claim 15 wherein said access means includes code entry means, memory means for recognizing a predetermined code entered into said entry means, and lock means responsive to said memory means upon recognition of said predetermined code for permitting said restricted access to the medications within said first and second canisters.

17. A medication dispensing system, comprising:
a first medication canister for receiving at least one scheduled medication for administration to a patient in accordance with a prescribed time schedule;
a second medication canister for receiving at least one unscheduled medication for administration to the patient on an as needed basis;
a dispensing unit for individual association with the patient and including first locking means for releasable locked reception of said first and second canisters;
code entry means associated with said dispensing unit;
memory means associated with said dispensing unit and said code entry means, said memory means recognizing entry of a first predetermined code using said entry means and responding thereto to permit access to and operation of said first locking means for selectively locking and releasing said first and second canisters from said dispensing unit; and
second locking means for restricting access to the medications within said first and second canisters, said second locking means being releasable to permit limited access to predetermined medication within said first canister during each of a plurality of time windows at intervals corresponding with said prescribed time schedule, and to permit access to the medication within said second canisters;
said memory means recognizing entry of a second predetermined code using said entry means to permit access to and operation of said second locking means.

18. The medication dispensing system of claim 17 further including means for detecting removal of medication from said first and second canisters, said memory means being responsive to said detecting means to create a record of medication removal from said first and second canisters.

19. A medication dispensing unit, comprising:
a housing for individual association with a patient and having first and second chambers formed therein;
a first medication canister for receiving at least one scheduled medication for administration to the patent in accordance with a prescribed time schedule, said first canister being receivable into said first housing chamber;
a second medication canister for receiving at least one unscheduled medication for administration to the patient on an as needed basis, said second canister being receivable into said second housing chamber;

programmable memory means for receiving and storing information regarding the medications received in said first and second housing chambers;

locking means for permitting limited access to the medications within said first and second canisters;

code entry means for manual entry of predetermined personnel identification codes;

said memory means including means for recognizing one of said identification codes and for responding thereto to permit access to the medication within said second canister and to permit limited access to a single dose of the medication within said first canister within a time window and at an interval corresponding with prescribed time schedule; and further including means for preventing reception of said first canister into said second housing chamber and for preventing reception of said second canister into said first housing chamber.

20. The medication dispensing unit of claim 19 further including alarm means, said alarm means being activated by said memory means at the beginning of said time window.

21. The medication dispensing unit of claim 20 wherein said memory means includes a clock.

22. The medication dispensing unit of claim 19 wherein said code entry means comprises a keyboard on said housing.

23. The medication dispensing unit of claim 19 further including means for detecting and displacing the rotational position of said second canister carousel.

24. The medication dispensing unit of claim 19 further including means for programming said memory means.

25. A medication dispensing unit, comprising:
a housing for individual association with a patient and having first and second chambers formed therein;
a first medication canister for receiving at least one scheduled medication for administration to the patent in accordance with a prescribed time schedule, said first canister being receivable into said first housing chamber;
a second medication canister for receiving at least one unscheduled medication for administration to the patient on an as needed basis, said second canister being receivable into said second housing chamber;
programmable memory means for receiving and storing information regarding the medications received in said first and second housing chambers;
locking means or permitting limited access to the medications within said first and second canisters; and
code entry means for manual entry of predetermined personnel identification codes;
said memory means including means for recognizing one of said identification codes and for responding thereto to permit access to the medication within said second canister and to permit limited access to a single dose of the medication within said first canister within a time window and at an interval corresponding with prescribed time schedule;
said first and second canisters each comprising a generally circular carousel having an annular outer tray, a magazine defining a generally annular array of cassettes for receiving the medication in individual doses, said magazine being supportable upon said cassette tray, a cover for locking engagement with said carousel in overlying relation with said magazine and having an access opening therein to expose one of said cassettes, and means for rotating said carousel beneath said cover.

26. The medication dispensing unit of claim 25 wherein each of said cassettes includes a hinged lid.

27. The medication dispensing unit of claim 25 wherein said cassettes of each of said magazines are interconnected by fragile membranes, said carousel tray including means for breaking said membranes to separate said cassettes upon installation of said magazines onto their respective carousel trays.

28. The medication dispensing unit of claim 25 wherein said locking means includes means for releasibly permitting unidirectional rotation of said carousels to displace said cassettes beneath the associated access opening upon entry of said one of said identification codes, said locking means further limiting said unidirectional rotation of said carousel associated with said first canister to displace the next cassette in rotational sequence beneath the associated opening and then to relock said first canister carousel against further rotation.

29. The medication dispensing unit of claim 28 further including a hinged door movable between a closed position covering said access opening of said second canister and an open position exposing said second canister access opening, said memory means being further responsive to entry of said one of said identification codes to permit movement of said door from said closed position to said open position.

30. A medication dispensing unit, comprising:
a housing for individual association with a patient and having first and second chambers formed therein;
a first medication canister for receiving at least one scheduled medication for adminstration to the patent in accordance with a prescribed time schedule, said first canister being receivable into said first housing chamber;
a second medication canister for receiving at least one unscheduled medication for administration to the patient on an as needed basis, said second canister being receivable into said second housing chamber;
said medication canisters each having a plurality of cassettes for receiving medication in individual doses;
programmable memory means for receiving and storing information regarding the medications received in said first and second housing chambers;
locking means for permitting limited access to the medications within said first and second canisters;
code entry means for manual entry of predetermined personnel identification codes;
said memory means including means for recognizing one of said identification codes and for responding thereto to permit access to the medication within said second canister and to permit limited access to a single dose of the medication within said first canister within a time window and at an interval corresponding with prescribed time schedule; and
further including means for detecting removal of one of said cassettes from either of said first and second canisters, said memory means being responsive to said detecting means to create a record of said cassette removal.

31. A method of dispensing medications to a patient, comprising the steps of:
loading at least one scheduled medication into a first canister, the scheduled medication being for administration to the patient in accordance with a prescribed time schedule;

loading at least one unscheduled medication into a second canister, the unscheduled medication being for administration to the patient on an as needed basis;

locking the first and second canisters into a dispensing unit which cooperates with the canisters to limit access to the medications therein; and entering one of a plurality of predetermined identification codes into a dispensing unit memory which responds upon recognition thereof to permit access to a single dose of the scheduled medication during limited time windows at predetermined intervals and to permit access to the unscheduled medications.

32. The method of claim 31 wherein said canister loading steps are performed at a central pharmacy area, said loading steps including loading a plurality of sets of the first and second canisters for respective locking into a corresponding plurality of dispensing units associated with individual patients.

33. The method of claim 32 wherein said loading steps include inputting patient identification and canister medication loading data into a main records computer, and further including the steps of transferring selected portions of said data to the dispensing unit memory of each of said dispensing units.

34. The method of claim 33 wherein said transferring step includes down-loading said selected data portions into a portable data transmission device and up-loading said selected data portions into said memory.

35. The method of claim 33 further including the step of detecting removal of medication from either of the canisters, and signalling the dispensing unit memory regarding such medication removal to create a record thereof.

36. The method of claim 35 further including the step of transferring the created medication removal record to the main records computer.

37. A method of dispensing medications to a patient, comprising the steps of:

loading at least one scheduled medication into a first canister, the scheduled medication being for administration to the patient in accordance with a prescribed time schedule;

loading at least one unscheduled medication into a second canister, the unscheduled medication being for administration to the patient on an as needed basis;

locking the first and second canisters into a dispensing unit which cooperates with the canisters to limit access to the medications therein; and entering one of a plurality of predetermined identification codes into a dispensing unit memory which responds upon recognition thereof to permit access to a single dose of the scheduled medication during limited time windows at predetermined intervals and to permit access to the unscheduled medications;

the first and second canisters each including an annular array of medication-containing cassettes supported for rotation beneath a cover having an access opening therein, and further including the steps of accessing the scheduled medication by unidirectional rotation of the canister cassettes to rotate the next cassette in sequence to a position beneath the access opening and then locking the first canister cassette against further rotation, and accessing the unscheduled medication by rotating the second canister cassettes to align a selected cassette beneath the associated access opening.

* * * * *